United States Patent [19]

Rankin

[11] 3,947,573
[45] Mar. 30, 1976

[54] OPTHALMIC SOLUTION
[75] Inventor: Billy F. Rankin, Rockville, Md.
[73] Assignee: Burton, Parsons and Company, Inc., Washington, D.C.
[22] Filed: Oct. 18, 1974
[21] Appl. No.: 516,089

Related U.S. Application Data

[60] Division of Ser. No. 324,983, Jan. 19, 1973, Pat. No. 3,856,919, which is a division of Ser. No. 44,564, June 8, 1970, Pat. No. 3,767,788, which is a continuation-in-part of Ser. Nos. 881,336, Dec. 1, 1969, abandoned, and Ser. No. 773,947, Nov. 6, 1968, abandoned.

[52] U.S. Cl. .................... 424/80; 424/78; 424/269
[51] Int. Cl.² ........................................ A61K 31/79
[58] Field of Search ................................ 424/78, 80

[56] References Cited
UNITED STATES PATENTS

| 3,311,577 | 3/1967 | Rankin | 424/80 |
| 3,755,561 | 8/1973 | Rankin | 424/78 |
| 3,767,788 | 10/1973 | Rankin | 424/78 |

Primary Examiner—Norman A. Drezin
Attorney, Agent, or Firm—Fidelman, Wolffe & Waldron

[57] ABSTRACT

An ophthalmic solution is provided for treatment of "dry eye", providing lubricating and cushioning effects for traumatized eyes, including trauma caused by the wearing of hard or gel-type contact lenses, and as a carrier for ophthalmic medicaments. The solution is an aqueous solution of polyethylene oxide, optionally polyethylene glycol, and other optional ingredients.

13 Claims, No Drawings

OPTHALMIC SOLUTION

This application is a Division of applicant's copending application Ser. No. 324,983, filed Jan. 19, 1973 now U.S. Pat. 3,856,919 which is a division of Ser. No. 44,564, filed June 8, 1970 now U.S. Pat. No. 3,767,788 which is a continuation in part of Ser. No. 881,336 filed Dec. 1, 1969 and Ser. No. 773,947, filed Nov. 6, 1968, both now abandoned.

The present invention relates to a multi-functional ophthalmic solution designed for and adapted to general use in the eyes of humans and domestic animals. The present invention further relates to a provision of a synthetic mucous layer which serves as a wetting agent in the eye, i.e. an artificial tear material useful for the treatment of both "dry-eye" or as a cleaning, lubricating, and cushioning agent for the eye after an injury or therapeutic surgery. The invention also relates to the utilization of the ophthalmic solution as a carrier for ophthalmic medicaments. Still further, the invention relates to an ophthalmic solution useful as a cleaning, lubricating, and cushioning agent for both hard and gel-type contact lenses. The invention also relates to the attainment of all the foregoing functions without optical interference, and with a solution which may be readily buffered to any convenient pH. The invention further relates to an ophthalmic solution having bactericidal activity.

Heretofore, ophthalmic solutions have generally conformed to the general specifications required for all such intended utilizations in the treatment of the eye. Such solutions have generally been isotonic, buffered to the required pH, sterile, and have contained additives for improved viscosity and longer retention in the eye. However, with many of such solutions, the problems of dosage, irritation to the eye, stability, and occular response persist.

Many attempts have been made to resolve these problems by modifying existing formulas, using different forms of eye-treating substances, or using bases immiscible with aqueous solutions. Such attempts have added little to the performance qualities of the products.

It is accordingly an object of the present invention to provide a multipurpose ophthalmic solution, suitable for general utilization in the eye of both humans and domestic animals. A further object of the present invention is the provision of such solutions which can be readily modified for particular purposes and utilizations, including the introduction into the eye, and the retention therein, of ophthalmic medicaments, the provision of a wetting agent, which serves an artificial tear for the treatment of "dry-eye", or a cushioning or lubricating agent for an injured or surgically treated eye, as a cleaning, lubricating and cushioning agent for utilization in conjunction with both hard and gel-type contact lenses, and the like.

These and still other objects, as will become apparent, from the following disclosure are attained by the composition of the present invention, which in its broadest terms comprises a polyethylene oxide polymer having a molecular weight of from about 100,000 to about 5,000,000, and, optionally, a polyalkylene glycol, preferably polyethylene glycol or polypropylene glycol, having a molecular weight of about from 400 to 6,000, and water.

Polyethylene oxide is known to exhibit excellent lubricating characteristics in aqueous solution and is freely soluble in water without degradation or hydrolysis. Wide ranges of molecular weights are available, and in the present invention, can be from 100,000 up to several million, e.g. 5,000,000 or even greater. The higher molecular weight materials are preferred in the present invention, and a range of 3,000,000 to 5,000,000 has been found particularly useful. Most preferred is a polyethylene oxide having a molecular weight of about 4,000,000. Such resins have extraordinary thickening action in water, even in the presence of salts. The thickening power increases sharply with both concentration and molecular weight. Thus, to attain the desired viscosity, substantially less ethylene oxide polymer is required for a relatively higher weight than would be the case when a lower molecular weight polymer is utilized. In addition, the higher molecular weights result in a higher strength lubricating film in solutions due to orientation of polymer molecules. The concentration of the ethylene oxide polymer will vary in the present invention with the molecular weight to provide a viscosity of from 0 to about 30,000 cps at 20°C. as measured by Brookfield Viscosimeter, where viscosities of from 0 to about 200 cps being measured using the ultra low viscosity adaptor rotated at a speed of 0.6 rpm, and viscosities greater than about 200 cps are measured with a number 6 spindle rotated at 10 rpm. Such viscosities will ordinarily be obtained when the concentration is within the range of about 0.05 to 2.0 weight per cent, depending upon the molecular weight of the polymer employed. With lower viscosities, whether due to lower molecular weight polymers or lower concentration, or both, inferior lubrication results, while higher viscosities result in difficult handling properties and characteristics, including insufficient flowability for full effective utilization in the eye.

The high molecular weight ethylene oxide polyethers utilized in the present invention can be conveniently prepared in the presence of a catalyst and an organic diluent in which the ethylene oxide monomer is soluble and the polymeric product is insoluble. During polymerization, the polymer chain grows through addition of the ethylene oxide monomer to an alkene oxide radical derived from previously reacted monomer units. The resultant materials are granular, tough, water soluble polymers which can range in molecular weight from about 10,000 to 5,000,000 or even more. The specific technique for producing these polymers are well-known to the art and form no part of the present invention.

Aqueous solutions of the polyethylene oxide resins have a low level of oral toxicity and an extreme level of compatibility in contact with the skin or in the eye. They are also characterized by high level of pituitousness and an extraordinarily high degree of pseudo-plasticity. The solutions are highly stable through a wide range of temperatures and can tolerate extremely wide variations in pH. Since the resins are non-ionic, their solutions undergo predictable salting effects and the inclusion of salts depresses the upper temperature limit of solubility and tends to reduce solution viscosities. The salting out effect is mild in comparison with that observed in the case of poly-electrolytes, but is comparable with that observed to other neutral molecules dissolved in high di-electric media. As a consequence, solutions of relatively low concentration of resin, on the order of those contemplated in the present invention, can tolerate substantial amounts of both organic and inorganic salts.

Because of the strong hydrogen-bonding affinity of the ether oxygen in the polyethylene oxide chain, the resin solutions will form association complexes with a wide variety of materials. Such associations complexes per se often exhibit properties markedly different from either component alone, but it has been found that the resin will give up associated materials when introduced into the eye. The dissociation in vivo may result from a salting out effect produced by the materials with which the solutions are contacted, e.g. various salts occuring in tears and the like.

Because of the high levels of pseudo-plasticity and pituitousness of polyethylene oxide aqueous solutions, it is highly desirable to include in the solution a material which will render a plasticizing effect. In addition, it is also desirable to include a humectant which will enhance fluid retention over the course of long term usage in the eye. These functions are provided by the inclusion in the solution of a polyalkylene glycol. The preferred polyalkylene glycol is polyethylene glycol, such as the Carbowaxes, as supplied by Carbide and Carbon Chemicals Company. Such materials have molecular weights ranging from about 400 up to as much as about 6000. Particularly preferred in the compositions of the preferred invention is polyethylene glycol having molecular weight of about 4000, although this preference is primarily because of the ready availability and convenience of processing of the particular material. Polyglycols containing other alkylene groups can also be utilized, such as polypropylene glycols and the like, but such materials are often not readily available, and for this reason alone are not particularly preferred in the present invention. The polyalkylene glycol can be present in amounts ranging up to 5000 preferably 500 to 5000, weight per cent based on the weight of the ethylene oxide polymer. Less than about 100% by weight can result in insufficient water retention and plasticizing effect, with concomittent drying of the eye and irritation of ocular tissue, while amounts greater than about 5000 weight per cent can exhibit a "salting out" effect, with the formation of waxy solid globules or particles which can be irritating to ocular tissue.

The basic ophthalmic solution of the present invention, i.e. the aqueous solution of polyethylene oxide and polyalkylene glycol, is useful per se in a number of contexts. Primary among these is the provision of a synthetic mucuous layer, which serves to clean and lubricate the eye, serving as a wetting agent and artificial tear for the treatment of "dry-eye" or to provide a cushioning and lubricating effect in an injured or surgically treated eye. A related effect is the cleaning, lubricating, and cushioning effects attained when the solution of the present invention is used in conjunction with contact lenses, of both the hard resin and gel type. Representative of the problems generally applicable to each of the foregoing usages, is the use of the ophthalmic base solution of the present invention in conjunction with gel-type contact lenses, and accordingly the use of the solution will be discussed with particular reference thereto.

The advent of the gel contact lens has generated entirely new requirements for contact lens treating solutions, and entirely new problems in hygenic handling and care for the lenses. In contrast to the more common hard type lens, usually made of polymethylmethacrylate, the gel lens will absorb relatively large proportions of water to form a soft, pliable material which has a tendency to fray. The gel is a three-dimensional lattice formed by the polymerization of glycol esters and diesters of acrylic acids. The glycol moieties of the molecules imparts a strong hydrophillic character to the lattice, with the consequent ability to absorb rather large amounts of water. By utilizing the unique properties of these lenses, new therapeutic options are presented for the treatment of ocular debilities. Since the lens per se represents only the environment of use of the composition, a more complete discussion of its physical parameters need not be repeated here. A discussion of the gel contact lens, including both the preparation and use thereof, occurs in Augenoptika, Heft 6, 1964, pages 5 and 6, which reports a paper delivered by Maximillian Dreyfus at the 15th WVA annual meeting.

One characteristic peculiar to the gel lens is the requirement that treating solutions contain no component that can become entrained in the lattice of the gel, since such materials tend to accumulate and become irritating to the ocular tissue. The lens does, however, require a cleaning and lubricating solution to cushion the ocular tissue from direct contact with the lens. The requirement for a cleaning action is shared by the gel-type lens with hard lenses and with synthetic tears and other such ophthalmic solutions. The exposure of the eye to various atmospheric pollutants, such as smoke, dust, pollen, noxious and irritating gases and the like can create severe discomfort and irritation, particularly in situations where the pollutants collect in the natural or artificial tear film to persist for substantial periods of time to exert their irritating effects. In addition to the avoidance of material which can accumulate in the gel, the materials used must be compatible with the gel and with ocular tissue, and not interfere with the physiochemical balance of the precorneal films. The attainment of these objectives is illustrated by the following example:

EXAMPLE I

An ethylene oxide polymer having a molecular weight of about 4,000,000, (Union Carbide Polyox WSR 301) and polyethylene glycol having a molecular weight of about 4,000 (Carbowax 4,000) are dissolved in distilled water in the following proportions:

| Polyethylene glycol | Ethylene oxide polymer | Distilled water |
|---|---|---|
| 9.00 gms. | 0.30 gms. | 300.00 ml. |

The solution is utilized to clean and hydrate gel-type contact lenses by immersing each lens in sufficient of the solution to completely cover the lens. Full hydration is effected in about 1–10 minutes. At the end of the immersion, the lens is lightly rubbed between the fingers and rinsed with water. Each lens was examined and was found to be fully hydrated and optically clean. The lenses are then implaced in human eyes in conventional fashion and are left in place for periods of 12 to 17 hours without noticable irritation. In dry environments or drafts some subjects flush the lenses while in place with small increments of the solution, which is found to effectively clean and rehydrate the lenses, whereby the tolerance period of the subject is enhanced and any drying problem alleviated.

By comparison, conventional lens wetting solutions of types commercially available are found to provide inferior cleaning, and the bacteriocidal ingredients occlude in the lens and cause irritation of the occular tissues.

In addition to the foregoing tests, both the solution of the present invention and the above mentioned commercially available lens solution of U.S. Pat. No. 3,171,752 were tested for retention in the eye in the following fashion:

A minor amount of fluorescein dye was incorporated into each solution. One solution was placed in one eye, the other solution in the other eye, of a number of rabbits. Examination of the eyes using an ultra-violet light source gave a quantitative base measure of the amount of solution present. Periodic repetitions of the examination revealed that this solution was gradually lost in either case, but that the commercial solution was retained much less effectively. The eyes treated with the solution of this example retained at two hours the same amount of solution as did the eyes treated with the commercial solution at twenty-five minutes. Details of the fluorophotometric determination can be found in Waltman et al, *Investigative Ophthalmology* Vol. 9, No. 4, pp. 247-249, April, 1970.

In no case, including both the utilization of the gel-type contact lens in the human eye, or the solution alone in the eyes of the test rabbits, was any evidence of irritation of the eye found to result from the solution of the present example.

Another surprising aspect of the composition of the present invention, and of Example I is particular, is the bacteriocidal effect which has been observed, both in vitro and in vivo, with a number of bacteria particularly confirmed with *Bacillus subtilis*, *Candida albicans*, *Escherichia coli*, *Pseudomonas aeruginosa*, and *Staphylococcus aureus*. The reasons for such activity remain at present unclear and are not fully understood, and accordingly, no explanation for such activity can be offered at present.

In addition to the per se usefulness of the ophthalmic solution of the present invention, as illustrated in the foregoing Example I, the ophthalmic solution of the present invention finds an additional area of broad utility as a carrier for ophthalmic treating materials, such as medicaments, particularly those requiring an acid pH. The high effectiveness of the ophthalmic solution of the present invention is believed due to the strong hydrogen bonding affinity of the ether oxygen of the polyethylene oxide chain. When combined with the ophthalmic solution of the present invention, ophthalmic medicaments are found to exhibit a much greater retention on orbital tissue, and results in a longer duration of medicament activity. In addition, the degree of retention attained permits the use of smaller amounts of the eye treating substances than has been found heretofore possible while maintaining the necessary levels of effectiveness. Examples of medicaments with which the carrier can be used are:

Pilocarpine, HCl
Hydrocortisone USP (alcohol)
Hydrocortisone Acetate
Prednisolone Acetate and other Cortisones
Neomycin Sulfate
Bacitracin
Penicillin
Sulfamerazine
Sodium Sulfacetamide
Sulfadiazine
Sulfasoxozole and other sulfa derivatives
Scopolamine hydrobromide
Epinephrine Bitrartrate
Phenylephrine HCl or other derivatives
Prostigmin Bromide
Pilocarpine (any of the salts)
Idoxuridine
Antipyrine
Naphthazoline HCl
Antazoline Phosphate The foregoing list is intended to be merely exemplary, and as the list illustrates, the ophthalmic solution of the present invention can be utilized as a carrier for substances such as antibiotics, mydriatics, biotics, antihistamines, and the like. The amount of eye treating substances used with the composition of the present invention depends upon the nature of this substance or substances employed, and the response of the individual receiving treatment. Typically, up to 500% or even more, based on the weight of the polyethylene oxide, of the eye treating medicament can be used.

When the eye treating eye substance or substances are those requiring an acid pH, one or more acids can be present in amounts sufficient to maintain the solutions at a pH of less than 7 and as low as about 3. An example of an acid which can be used with eye treating substances such as medicaments requiring an acid pH is boric acid. However, many eye treating substances must be maintained in a basic or neutral medium, and, in these instances, one or more pH buffers such as sodium borate is added to maintain a solution of a neutral or slightly basic pH. Typically, the buffering substances present in an amount sufficient to maintain the pH at the desired level, are from between about 7.4 and about 8.2, and preferably at about 7.6. Other buffering compositions can be used as well, including a combination of phosphates such as, for example, mono-sodium phosphate and disodium phosphate to provide both acid and base control. Other phosphates, acetates, and carbonates can be substituted for the phosphates mentioned above, provided they are compatible with the eye. Specifically the amount of buffering additions can range from about 0 to 4%, preferably about 0.2%, for the dibasic component, and from about 0 to about 0.5% for the mono-basic component, where the percentages are by weight based upon the total weight of the overall composition, with the ratio of components balanced to provide proper pH for the overall composition.

The utilization of the ophthalmic solution of the present invention is the carrier for the ophthalmic medicaments is illustrated by the following example:

EXAMPLE II

The following composition is illustrative of the utilization of the composition of the present invention as a carrier for medicaments: an ethylene oxide polymer having a molecular weight of about 4,000,000 (Union Carbide Polyox WSR 301), and a polyethylene glycol having a molecular weight of about 4,000 (Carbowax 4,000), are dissolved in distilled water in the following proportions:

| | |
|---|---|
| Polyethylene glycol | 9.00 gm |
| Ethylene Oxide Polymer | 0.30 gm |
| Distilled Water | 300.00 ml |

To the base solution, there are then added 6.00 gm of pilocarpine HCl and 3.00 gm of boric acid. Both the salt and the acid dissolve readily in this solution.

The foregoing formulation is utilized in the treatment of glaucoma patients, who had previously required four standard pilocarpine treatments per day. It is found that two treatments with the formulation of the present invention provide the same therapeutic effects as the four standard treatments. Studies on normal eyes of both animals and humans, after the fashion indicated in Example I, showed no adverse effects after prolonged application periods, and a much longer period of retention in the eye for each application.

Whatever the contemplated utilization of the ophthalmic solution of the present invention, it can be desirable to include in the solution one or more of a variety of secondary additives, as hereinafter described in fuller detail. For example:

High compatible cellulose derivatives, of a variety soluble in water, such as, for example, methyl cellulose, hydroxyethyl cellulose, hydroxypropyl cellulose, carboxymethyl cellulose, hydroxypropyl methyl cellulose, and the like can be included in this solution to act as a mechanical buffer or as a viscosity controlling agent, and can be used to maintain the viscosity of the overall composition within the desired range as hereinbefore described. Specifically, the cellulose derivatives, when employed, should be present in an amount sufficient to maintain viscosity of the overall composition at the desired level.

The composition of the invention can also contain one or more eye compatible biocides, such as thimerosal (sodium ethylmercurithiosalicuylate), and the di-, tri-, or tetrasodium ethylenediamine tetraacetates. The percentages of such biocides can vary over a broad range, but typically do not exceed about 1% by weight of the overall composition.

In addition, the composition of the present invention can also contain one or more eye compatible non-ionic surfactants in amounts varying over a wide range, but typically in amounts up to about 0.5% by weight, in order to provide product stability. An example of the surfactants which can be utilized are Tergitol 1559 (Carbide and Carbon Chmicals Co.); Pluronic F68 (Wyandotte Chemical Corp., Michigan Alkali Division); Tweens of H.L.B. value of 11 or higher (Atlas Powder Company).

Still another subsidiary component which can be added to the ophthalmic solutions of the present invention includes polyvinyl pyrrolidone (such as Plasdone C, supplied by Entira Chemicals, Division of GAF Corp.) which performs a number of desirable functions. Polyvinyl pyrrolidone (PVP) acts as a detoxicant, binding anti-toxins present in eye fluids, and rendering them harmless. PVP also acts to protect the solution by preventing its breakdown because of particle agglomeration, and acts as a demulcent lubricant by a combination of adhesive and lubricating properties which aid in the spreading of the viscous solution. The PVP also operates to prevent blepharospasm (involuntary eyelid contraction), but has little effect on an overall composition viscosity. PVP is desirably present in an amount of from 0.5 to 10.0 weight per cent based on the overall solution.

The foregoing illustrations of secondary additives for the ophthalmic solution of the present invention is intended to be merely exemplary of the more common of the additives to ophthalmic solutions well-known to those of ordinary skill in the art. It should accordingly be understood that such additives are not required for effective operation of the ophthalmic solution of the present invention, and nor is it intended by the enumeration of certain additives to exclude others.

While the ophthalmic solution of the present invention is readily formed by simply combining the ingredients, the polyethylene oxide material can occasionally present difficulties in readily dissolving. Such difficulties can be avoided by the utilization of the following technique: An increment of distilled water sufficient to dissolve the constituents of the composition is placed in a stainless steel container and heated to about 50°C. If a surfactant is included in a composition, it is dissolved first in distilled water by agitation, e.g. with a dispersing mixer which has a variable speed control set at low speed.

Any medicament, such as pilocarpine HCl, pH buffers, and the polyalkaline glycol, such as carbowax 4,000, and other additives such as biocides and the like are then dissolved with medium speed agitation in the water/surfactant mixture, following which the polyvinyl pyrrolidone is added with high-speed mixing and agitation. If a cellulosic derivative mechanical buffer is utilized, it is sifted slowly into the vortex created by the agitator at high speed. When the cellulosic substance is completely dispersed, the ethylene oxide polymer, such as Polyox Resin WSR 301, is sifted slowly into the vortex at high agitation, until the resin appears to be climbing up the agitator shaft, at which time the speed is reduced to 100 to 200 rpms. Agitation is then continued until the resin is completely dispersed in the solution, typically from 2 to 6 hours. Additional distilled water is then added to bring the solution up to volume. Because the resin can be precipitated out at high temperatures, the product may be sterilized after packaging by means of ethylene oxide gas sterilization. Containers for the solution are placed in racks in a gas autoclave, which draws a vacuum of about 24 ml of mercury, after which all air is replaced with an ethylene oxide freon mixture (12–88%) at 12 psi for 12 hours, and at relative humidity of 45 to 50%. It is also possible to sterilize in an autoclave if the conditions are controlled to minimize particle agglomeration of any resin which precipitates out. So long as agglomeration is not excessive, the resin will redissolve when the temperature is again reduced. Even when autoclaving temperatures are extreme and the time at temperature causes excessive agglomeration, the resin will redissolve, but at a slower rate.

EXAMPLE III

As an illustration of the composition of the present invention containing the aforementioned secondary additives, the following composition was prepared on a relatively large scale:

| | |
|---|---:|
| bacteriocide (Thimerosal, 10%) | 240 c.c |
| disodium phosphate | 1200 grams |
| polyethylene glycol (MW. 4,000) | 6000 grams |
| polyvinyl pyrrolidone | 30000 grams |
| disodium ethylenediamine-tetracetate | 600 grams |
| non-ionic surfactant | 132 grams |
| hydroxy ethyl cellulose (MW 52,000) | 3000 grams |
| polyethylene oxide (MW 4,000,000) | 3000 grams |
| distilled water | 150 gallons |

The solution formed from the foregoing components was clear and free of polymer globules, and was found to have a pH of about 7.3 and a viscosity of about 150 cps.

The solution was utilized as a wetting, cleaning, and cushioning medium by a number of patients using hard-type, polymethyl methacrylate contact lenses. With patients who had previously worn the lenses, greater comfort and tolerance were reported, even by those who had previously experienced difficulty with the lenses. Most patients reported that they were able to wear their lenses for greater periods of time than had previously been possible, regardless of the type of wetting solution they had used before. With patients who had not previously worn contact lenses, the solution of the present invention dramatically reduced the problems of lens delivery and greatly accelerated the adaptation of the patients to the use of the lenses. In all the trials, no adverse side effects or irritation was noted either subjectively or by clinical examination.

It has been noted that in the utilization of the ophthalmic solution of the present invention with contact lenses, certain ranges of viscosity provide better results than others. For example, with hard-type lenses, the best results are attained at a viscosity of about 30 to 200 cps, and that range is accordingly preferred for such usage. The most preferred viscosity for use with hard-type lenses is about 150 cps. With the gel-type lens, the most effective, and hence the preferred viscosities lie in the range of about 0 to 30 cps, with values of about 10 being most preferred. No variation of effectiveness with viscosity has been noted when the solution is used as a carrier for medicaments or as a synthetic tear or the like.

It should be noted that a viscosity of zero as measured is a result of the limitations of the available techniques and apparatus, and does not represent such an anomaly as it might superficially appear. It should further be noted that all designations of viscosity appearing herein represent the values as obtained with the Brookfield Viscosimeter, where all values below 200 are obtained with the ultra low viscosity adapter rotated at 0.6 rpm and all values above 200 are obtained with a number 6 spindle at 10 rpm. For values ranging from about 175 to about 250 cps, results obtained by the two differing adaptations are generally comparable in the case of the present solutions.

EXAMPLE IV

A miotic composition was prepared containing the following components:

| | | |
|---|---|---|
| Pilocarpine HCl | 2.00 | wt.% |
| boric acid | 30.00 | grams |
| polyethylene glycol (M.W. 4,000) | 30.00 | grams |
| polyvinyl pyrrolidone | 150.00 | grams |
| benzalkonium chloride (17% solu.) | 0.66 | c.c. |
| disodium ethylenediaminetetracetate | 3.00 | grams |
| non-ionic surfactant | 0.60 | grams |
| hydroxy ethyl cellulose (M.W. 52,000) | 15.00 | grams |
| polyethylene oxide (M.W. 4,000,000) | 15.00 | grams |
| distilled water | 3000.00 | milliliters |

The solution, designated solution A, was administered to one eye of each of four patients to diminish the diameter of the pupil. At the same time, the other eye was treated with a conventional, 2 percent solution of Pilocarpine HCl in a commercially available ophthalmic solution of 1.4% polyvinyl alcohol and 0.5% chlorobutanol in water (Liquifilm Tears, Allergan) designated solution B. Measurements of pupil diameter were taken periodically as shown in Table I.

Table I

| Patient | A | | B | | C | | D | |
|---|---|---|---|---|---|---|---|---|
| Eye | L | R | L | R | L | R | L | R |
| Time, Hours | | | | | | | | |
| 0 | 5.0 | 4.6 | 7.3 | 6.9 | 7.1 | 7.7 | 6.3 | 5.8 |
| 0.5 | 1.7 | 3.0 | 1.5 | 1.2 | 1.4 | 3.4 | 2.2 | 1.2 |
| 1.0 | 2.3 | 3.3 | 2.0 | 1.1 | 1.6 | 3.8 | 2.5 | 1.8 |
| 2.0 | | | | | 2.0 | 5.6 | | |
| 2.5 | 3.5 | 4.3 | 3.6 | 2.6 | | | 2.6 | 1.5 |
| 3.0 | 3.4 | 4.1 | 4.1 | 2.9 | 2.4 | 5.5 | 3.2 | 2.0 |
| 4.0 | 3.8 | 4.1 | 3.5 | 2.6 | 3.1 | 6.3 | 3.8 | 2.1 |
| 5.0 | 4.2 | 4.5 | 3.7 | 3.1 | 3.7 | 7.3 | 3.7 | 2.6 |
| 6.0 | 4.6 | 4.9 | 4.9 | 4.1 | 4.6 | 6.6 | 4.2 | 2.6 |
| Solution | A | B | B | A | A | B | B | A |

EXAMPLE V

A mydriatic dilator composition was prepared, the same as the composition of Example IV, with the exception that the Pilocarpine HCl was replaced by 5 percent by weight phenylephrine, and compared in the same manner with a 5 percent solution of phenylephrine in the PVA carrier used in Example IV. The results are reported in the following Table II, where again A represents the composition of the present example and B represents the commercially available solution of the prior art.

Table II

| Patient | A | | B | | C | | D | |
|---|---|---|---|---|---|---|---|---|
| Eye | L | R | L | R | L | R | L | R |
| Time, hours | | | | | | | | |
| 0 | 3.1 | 3.6 | 4.9 | 4.9 | 5.2 | 5.8 | 3.6 | 3.8 |
| 0.5 | 5.6 | 3.7 | 6.2 | 7.2 | | | 3.5 | 4.0 |
| 1.0 | | | | | 8.1 | 6.0 | | |
| 1.5 | 6.4 | 4.1 | 5.2 | 6.9 | 7.6 | 5.0 | 4.0 | 4.6 |
| 2.5 | 6.2 | 4.8 | 5.3 | 5.6 | 7.9 | 6.2 | 4.1 | 5.6 |

Table II-continued

| Patient | Pupil Diameter, m.m. | | | | | | | |
|---|---|---|---|---|---|---|---|---|
| | A | | B | | C | | D | |
| Eye | L | R | L | R | L | R | L | R |
| 3.75 | 5.5 | 3.6 | 4.8 | 5.8 | 7.0 | 6.1 | 3.0 | 3.8 |
| 4.75 | 3.5 | 3.5 | 4.5 | 5.1 | 5.4 | 5.3 | 3.1 | 3.5 |
| Solution | A | B | B | A | A | B | B | A |

A further example of the effectiveness of the composition of the present invention occurs primarily in the area of ophthamologic diagnosis, where it is conventional to apply fluorescein, or a comparable material, dissolved in a carrier, to the eye and after allowing the dye to penetrate the tissues of the eye, to conduct an examination by visual inspection with the aid of an ultra-violet light source, which causes the dye to fluoresce. It has been found that when the ophthalmic solution of the present invention is utilized as the carrier, the dye is absorbed in substantially greater proportions and at a much faster rate than has been possible with the compositions of the prior art. Accordingly, solutions of fluorescent dyes in the ophthalmic solution of the present invention is of great aid in the examination of the eye.

While certain specific considerations have been disclosed and discussed herein, such have been offered solely to exemplify the present invention, and should in no way be construed as limiting. The proper scope and nature of the invention is set forth in the following claims.

What is claimed is:

1. An opthalmic solution consisting essentially of an aqueous solution of an ethylene oxide polymer, having a molecular weight of at least about 100,000, in an amount of from about 0.05 to 2.0 weight percent sufficient to provide a viscosity of from about 0 to 30,000 cps, from about 100 to about 5,000 weight percent, based on the ethylene oxide polymer, of a lower polyalkylene glycol, having a molecular weight from about 400 to about 6,000 and from .5 to 10 percent polyvinyl pyrrolidone based on the weight of the overall solution, said composition further including a therapeutically effective amount up to about 500 weight percent, based on the weight of the ethylene oxide polymer of an opthalmic medicament.

2. The composition of claim 1 wherein said ethylene oxide polymer has a molecular weight of about 3,000,000 to 5,000,000.

3. The composition of claim 1 wherein said ethylene oxide polymer has a molecular weight of about 4,000,000.

4. The composition of claim 1 wherein said polyalkylene glycol is polyethylene glycol.

5. The composition of claim 4 wherein said polyethylene glycol has a molecular weight of from about 400 to 6,000.

6. The composition of claim 4 wherein said polyethylene glycol has a molecular weight of about 4,000.

7. The composition of claim 1 wherein said aqueous solution further comprises an effective amount of an eye compatible pH buffer.

8. The composition of Claim 7 wherein said buffer is boric acid.

9. The composition of claim 7 wherein said buffer is a combination of mono-sodium and di-sodium phosphates.

10. The composition of claim 1 wherein said aqueous solution further comprises a mechanical buffer selected from the group consisting of methyl cellulose, hydroxyethyl cellulose, hydroxypropyl cellulose, carboxymethyl cellulose, hydroxypropyl methyl cellulose, and mixtures thereof.

11. The composition of claim 1 wherein said aqueous solution further comprises up to about 1 percent by weight of an eye compatible biocide.

12. The composition of claim 1 wherein said aqueous solution further comprises up to about 0.5 percent by weight of an eye compatible non-ionic surfactant.

13. The composition of claim 1, wherein the opthalmic medicament is pilocarpine HCl.

* * * * *